US010179190B2

(12) United States Patent
Nagale et al.

(10) Patent No.: US 10,179,190 B2
(45) Date of Patent: Jan. 15, 2019

(54) COMPOSITIONS AND METHODS FOR TREATMENT OF TISSUE

(71) Applicant: Boston Scientific Scimed, Inc., Maple Grove, MN (US)

(72) Inventors: Sandra Nagale, Bolton, MA (US); David Shreeve, Northborough, MA (US); Mark Boden, Harrisville, RI (US); Jonathan Zoll, Brookline, MA (US); Timothy Harrah, Cambridge, MA (US); Steven Kangas, Woodbury, MN (US); Kasyap Seethamraju, Eden Prairie, MN (US); Deanna Cavallaro, Medford, MA (US); Martin Phelan, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 173 days.

(21) Appl. No.: 15/167,209

(22) Filed: May 27, 2016

(65) Prior Publication Data
US 2016/0346430 A1 Dec. 1, 2016

Related U.S. Application Data

(60) Provisional application No. 62/168,534, filed on May 29, 2015.

(51) Int. Cl.
*A61L 27/20* (2006.01)
*A61L 27/52* (2006.01)
(52) U.S. Cl.
CPC ............... *A61L 27/20* (2013.01); *A61L 27/52* (2013.01); *A61L 2400/06* (2013.01); *A61L 2430/22* (2013.01)
(58) Field of Classification Search
CPC ....... A61L 27/20; A61L 27/52; A61L 2400/06
USPC ............................. 514/54; 606/153
See application file for complete search history.

(56) References Cited

U.S. PATENT DOCUMENTS

| | | | |
|---|---|---|---|
| 6,428,802 B1 | 8/2002 | Atala | |
| 6,692,490 B1 | 2/2004 | Edwards | |
| 7,611,542 B2 * | 11/2009 | Bourne | A61F 2/0036 424/501 |
| 7,955,316 B2 | 6/2011 | Weitzner et al. | |
| 9,159,641 B2 | 10/2015 | Hobart et al. | |
| 2003/0171645 A1 | 9/2003 | Silverman et al. | |
| 2006/0070631 A1 | 4/2006 | Scopton et al. | |
| 2006/0190022 A1 | 8/2006 | Beyar et al. | |
| 2006/0247720 A1 | 11/2006 | Starkebaum | |
| 2007/0282184 A1 | 12/2007 | Roberts | |
| 2008/0051627 A1 | 2/2008 | Raju | |
| 2008/0125709 A1 | 5/2008 | Chang et al. | |
| 2008/0125804 A1 | 5/2008 | Gostout | |
| 2008/0154228 A1 | 6/2008 | Ortiz et al. | |
| 2009/0012469 A1 | 1/2009 | Nita | |
| 2009/0018603 A1 | 1/2009 | Mitelberg et al. | |
| 2010/0056989 A1 | 3/2010 | McKay | |
| 2010/0152704 A1 | 6/2010 | Lee et al. | |
| 2010/0198139 A1 | 8/2010 | Glickman | |
| 2010/0256594 A1 | 10/2010 | Kimmell et al. | |
| 2010/0268191 A1 | 10/2010 | Trudel et al. | |
| 2011/0124765 A1 | 5/2011 | Yang et al. | |
| 2011/0166516 A1 | 7/2011 | Orr | |
| 2013/0018281 A1 | 1/2013 | Nagale et al. | |
| 2013/0072855 A1 | 3/2013 | Sherry et al. | |
| 2013/0090640 A1 | 4/2013 | Nagale et al. | |
| 2013/0090648 A1 | 4/2013 | Nagale et al. | |
| 2014/0276590 A1 | 9/2014 | Hiller et al. | |
| 2014/0287003 A1 * | 9/2014 | Dill | A61K 31/167 424/400 |

FOREIGN PATENT DOCUMENTS

| | | |
|---|---|---|
| WO | WO 2012/013246 A1 | 2/2012 |
| WO | WO 2012/083155 A2 | 6/2012 |
| WO | WO 2013/039711 A2 | 3/2013 |

OTHER PUBLICATIONS

Mansfield et al. Comparison of Receptor Binding Characteristics of Commonly Used Muscarinic Antagonists in Human Bladder Detrusor and Mucosa. The Journal of Pharmacology and Experimental Therapeutics 328:893-899, 2009. (Year: 2009).*
"Core Technology," retrieved from Contura website at http://www.contura.com/products/core-technology on Dec. 28, 2012 (2 pages).
"Products: Tissue Repair," retrieved from Fidia website at http://fidiapharma.com/files/index.cfm?id_rst=137 on Dec. 28, 2012 (3 pages).
"Histology Fact Sheet: Urinary Bladder." Histology—World! Histology Fact Sheet—Urinary Bladder. Web. Jun. 2, 2016. http://histology-world.com/factsheets/bladder1.htm.
"Treatment of morbid obesity by intraparietogastric administration of botulinum toxin: a randomized, double-blind, controlled study" International Journal of Obesity (2007) 31, 707-712 (6 pages).
Andersson, K. Arner, A., (2004) Urinary Bladder Contradiction and Relaxation: Physiology and Pathophysiology, Physiol Rev. 84, 935-986.

(Continued)

*Primary Examiner* — Yih-Horng Shiao
(74) *Attorney, Agent, or Firm* — Bookoff McAndrews, PLLC

(57) ABSTRACT

Methods of treating tissue of a patient, e.g., tissue of an organ such that the bladder, are described. The methods may comprise inserting a medical device within the bladder; and injecting a composition to separate a first layer of tissue from a second layer of tissue. The composition may comprise at least one polysaccharide compound having a concentration ranging from approximately 0.05% to approximately 25% by weight, with respect to the total weight of the composition. The composition may at least partially separate the first layer of tissue from the second layer of tissue. At least one of the first layer of tissue or the second layer of tissue may be a detrusor muscle tissue.

19 Claims, 5 Drawing Sheets

(56) References Cited

OTHER PUBLICATIONS

Apostolidis et al., "Proposed Mechanism for the Efficacy of Injected Botulinum Toxin in the Treatment of Human Detrusor Overactivity," European Urology 49 (2009) pp. 644-650.
Canning, B.J., Spina, D., & Baron R. (2009). Sensory nerves. Dordrecht: Springer.
Chess-Williams, R., (2002) Urinary Bladder Contraction and Relaxation: Physiology and Pathophysiology, Physiol Rev. 84, 935-986.
Hillel, Alexander T., et al., "Photoactivated Composite Biomaterial for Soft Tissue Restoration in Rodents and in Humans," Science Translation Medicine, vol. 3, Iss. 93, p. 93ra67 (2011) (13 pages).
Karajanagi, Sandeep S., et al. "Assessment of Canine Vocal Fold Function After Injection of a New Biomaterial Designed to Treat Phonatory Mucosal Scarring," Annals of Otology, Rhinology & Laryngology, vol. 120, pp. 175-184 (2011), Abstract (1 page).
Lin-Yung-Chang, and Shi-Ming Tu. "Bladder Cancer." Physicians Practice (2005): 1-13. Web. Jun. 1, 2016.
Wang, K., Prasad, G., & Tian, J. (2010) Endoscopic muscosal resection and endoscopic submuscosal. Curr Opin Gastroenterol., 26, 453-458.
Xian, Jinhong et al., "Alerations of Gastrointestinal Motility in Obesity" Obesity Research vol. 12, No. 11, Nov. 2004, 1723-1732 (10 pages).
Lippincott Williams & Wilkins, (2007). Straight A's in Anatomy & Physiology, Philadelphia: Lippincott Williams & Wilkins.
SEER Training Moduels. (Jun. 23, 2009). Retrieved Nov. 20, 2014, from http://training.seer.cancer.gov/bladder/anatomy/layers.html.

* cited by examiner

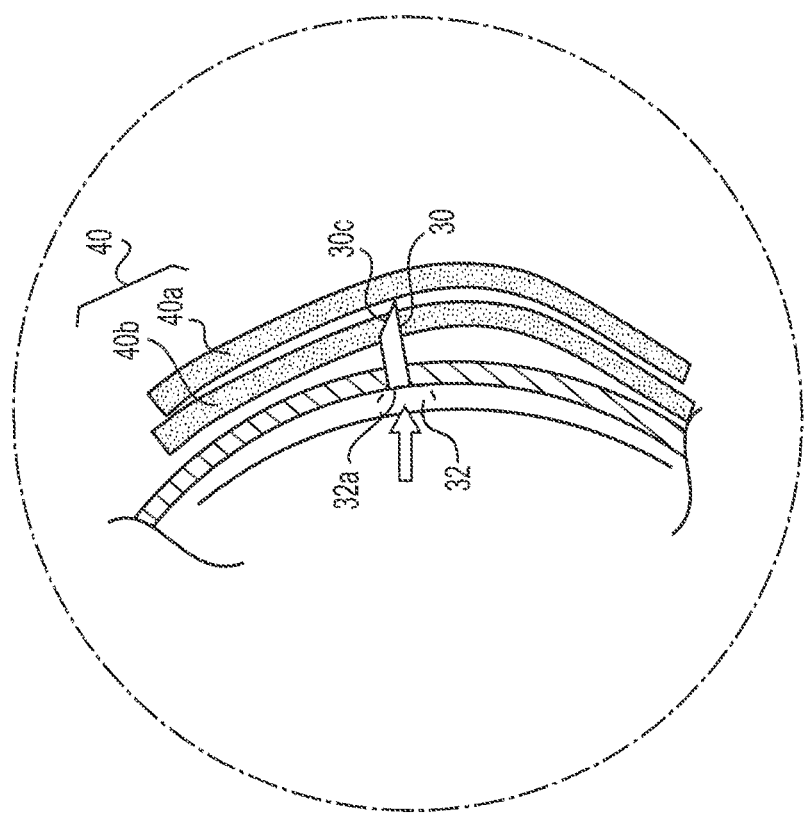
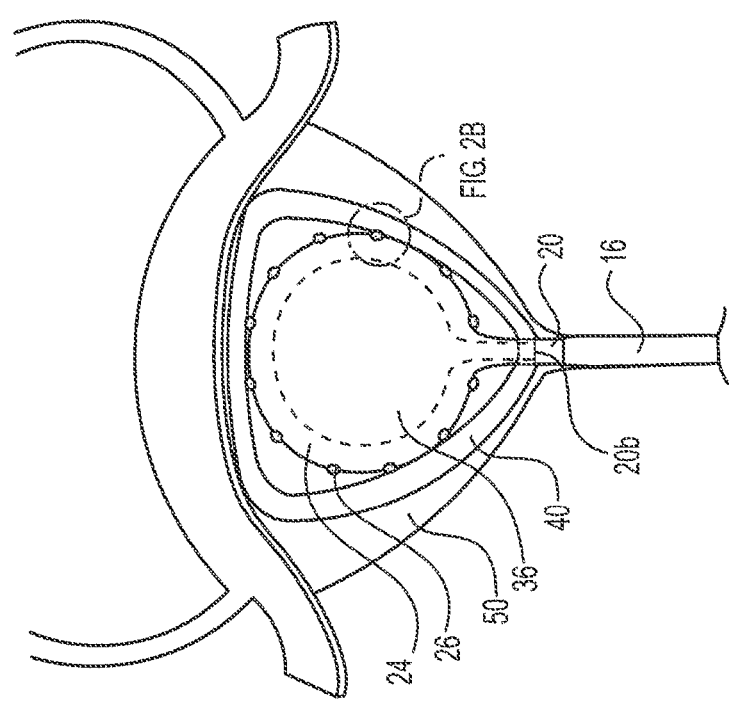
FIG. 2B
FIG. 2A

COMPOSITIONS AND METHODS FOR TREATMENT OF TISSUE

CROSS-REFERENCE TO RELATED APPLICATIONS

This patent application claims the benefit of priority under 35 U.S.C. § 119 to U.S. Provisional Patent Application No. 62/168,534, filed May 29, 2015, which is herein incorporated by reference in its entirety.

TECHNICAL FIELD

Aspects of this disclosure relate generally to compositions and methods of use thereof for treating tissue within a patient. In particular, aspects of the present disclosure relate to compositions and methods for treating tissue, e.g., bladder tissue.

BACKGROUND

Overactive Bladder ("OAB") is a urological condition that affects approximately 50 million patients worldwide. A patient suffering from OAB typically experiences sudden yet frequent and unstoppable urges to urinate, even though the bladder may contain only a small amount of urine. This condition is usually associated with frequent and spontaneous contractions of the detrusor muscle, which is located in the bladder wall and surrounds the bladder.

The etiology of OAB is unclear, and indeed there may be multiple possible causes. OAB, however, is most often associated with detrusor muscle overactivity (i.e., frequent and spontaneous contractions of the detrusor muscle). These frequent contractions may fuse into a global and sustained contraction resulting in an urge to urinate. A malfunctioning detrusor muscle may cause overactive bladder. Indeed, there is a body of evidence suggesting that, in comparison with healthy bladders, overactive bladders exhibit localized changes in detrusor muscle morphology. These changes likely originate from defects on cellular and multi-cellular levels and changes in the nervous system. Such nervous system changes have been correlated to the observed local pathological changes in the muscle (e.g., patchy denervation, increased amount of connective tissue between muscle bundles), which may contribute to the abnormal function of the detrusor muscle.

Recent evidence suggests that the detrusor muscle may be triggered by substances released from the bladder wall when the wall experiences stimulation, such as stretching of the bladder wall. The released substances may include adenosine triphosphate ("ATP"), prostaglandins ("PG"), nitric oxide ("NO"), acetylcholine ("Ach"), and nerve growth factor ("NGF"). The release of these chemicals has been linked to over-expression of multiple receptors (muscarinic and cholinergic receptors, TRPV, etc.) and abnormally triggering the nerves (e.g., triggering increased bladder contractions in an OAB). Thus, there is a need to attenuate or block this communication. Targeting receptors with systemic drugs, however, may cause side effects, including adverse effects to other areas of the body carrying those receptors. For example, in addition to the urinary tract, muscarinic receptors and other types of receptors reside in other organs such as the heart, salivary glands, gastrointestinal tract, eyes, heart, and brain.

SUMMARY

Aspects of the present disclosure provide methods and compounds for treatment of tissue.

In one aspect, the invention provides a composition for treatment of an organ of a patient. The composition may comprise at least one polysaccharide compound comprising at least one of xanthan gum, alginate, carboxymethyl cellulose, glycosaminoglycan (such as, e.g., heparin or hyaluronic acid, among other glycosaminoglycans), pectin, chitosan, a salt thereof, or any combination thereof, wherein the polysaccharide comprises from approximately 0.05% to approximately 25% by weight or from approximately 0.25% to approximately 5% by weight, with respect to the total weight of the composition, wherein the composition is formulated for injection, the composition having a first viscosity before injection into the organ, and a second viscosity higher than the first viscosity after injection into the organ.

Examples of the composition may additionally and/or alternatively include one or more other features. For example, the at least one polysaccharide compound may comprise xanthan gum having a concentration ranging from approximately 0.1% to approximately 1% by weight, with respect to the total weight of the composition. The concentration of xanthan gum in the composition may be approximately 0.65% by weight, with respect to the total weight of the composition. The composition may have an endotoxin content of less than 400 Endotoxin Units. The composition may comprise at least one calcium compound, or another divalent or multivalent cationic species. The at least one calcium compound may be chosen from calcium carbonate, calcium chloride, calcium alginate, hydroxyapatite, or any combination thereof. The at least one polysaccharide may comprise alginate, and a molar ratio of the calcium compound to alginate ranges from about 1:1 to about 1:3. The molar ratio of the calcium compound to alginate may be about 1:2. The composition may comprise alginate particles having a mean diameter ranging from about 100 μm to about 1 mm, such as from about 300 μm to about 500 μm. The concentration of alginate may range from approximately 1.5% to approximately 2.5% by weight, with respect to the total weight of the composition. The composition may further comprise at least one crosslinking agent. The composition may be formulated to form a gel less than 20 minutes after injection. The composition may be formulated to form a gel between about 5 minutes and about 15 minutes after injection. The organ may be a bladder. The treatment may be of overactivity of the bladder.

In another aspect, a method of treating tissue of a patient may include injecting a composition between a first layer of tissue and a second layer of tissue of an organ, wherein the composition may comprise at least one polysaccharide compound or a salt thereof having a concentration ranging from approximately 0.05% to approximately 25%, or from approximately 0.25% to approximately 5% by weight, with respect to the total weight of the composition, wherein the composition at least partially separates the first layer of tissue from the second layer of tissue.

Examples of the method may additionally and/or alternatively include one or more other features. For example, the organ may be a bladder. The least one of the first layer or the second layer of tissue may be detrusor muscle tissue. The contraction of the detrusor muscle may be reduced after the composition is injected. The composition may have a first viscosity before injection into the organ, and a second viscosity higher than the first viscosity after the composition is injected into the organ. The at least one polysaccharide compound may be chosen from glycosaminoglycans (such as, e.g., heparin or hyaluronic acid, among other glycosaminoglycans)xanthan gum, alginate, carboxymethyl cellulose, chitosan, pectin, a salt thereof, or a combination thereof. The at least one polysaccharide compound may comprise xanthan gum having a concentration ranging from approximately 0.1% to approximately 1% by weight, with respect to the total weight of the composition. The at least one polysaccharide compound may comprise alginate, and wherein the composition may further comprise at least one calcium compound. A molar ratio of the calcium compound to the at least one polysaccharide compound may range from about 1:1 to about 1:3.

In another aspect, a method of treating a bladder of a patient may include injecting a composition between a first layer of tissue and a second layer of tissue of the bladder, wherein the composition may comprise at least one polysaccharide compound chosen from xanthan gum, alginate, or a combination thereof, the concentration of the at least one polysaccharide compound ranging from approximately 0.05% to approximately 25% by weight, or from approximately 0.25% to approximately 5% by weight, with respect to the total weight of the composition, wherein the composition may at least partially separate the first layer of tissue from the second layer of tissue.

Examples of the method may additionally and/or alternatively include one or more other features. For example, the first layer of tissue may be a mucosal layer, and the second layer of tissue may be a muscle layer. The composition may comprise alginate, and wherein the composition may further comprise a calcium compound, the composition having a molar ratio of calcium compound to alginate of about 1:2. The composition may comprise calcium alginate. The method may further comprise mixing the at least one polysaccharide compound with a second component of the composition less than approximately 20 minutes before injecting the composition. The method may further comprise detecting a location of abnormal function of the bladder and injecting the composition at the location, wherein the location includes the first and second layers of tissue.

In another aspect, a method of treating a bladder of a patient may include injecting a composition between a first layer of tissue and a second layer of tissue of the bladder, wherein the composition may comprise at least one polysaccharide compound having a concentration ranging from approximately 0.05% to approximately 25% by weight, or from approximately 0.25% to approximately 5% by weight, with respect to the total weight of the composition; wherein the composition may at least partially separate the first layer of tissue from the second layer of tissue; and wherein at least one of the first layer of tissue or the second layer of tissue may be detrusor muscle tissue.

Examples of the method may additionally and/or alternatively include one or more other features. For example, the at least one polysaccharide compound may be chosen from xanthan gum, alginate, carboxymethyl cellulose, glycosaminoglycan (such as, e.g., heparin or hyaluronic acid, among other glycosaminoglycans), chitosan, pectin, a salt thereof, or a combination thereof. The composition may have a first viscosity before injection into the bladder, and a second viscosity higher than the first viscosity after injection into the bladder. The composition may form a gel between the first tissue layer and the second tissue layer. The composition may form a gel within about 20 minutes after injection into the bladder.

Additional objects and advantages of the disclosure will be set forth in part in the description, which follows, and in part will be evident from the disclosure, or may be learned by practice of the disclosed subject matter. The objects and advantages of the disclosed subject matter will be realized and attained by means of the elements and combinations particularly pointed out in the appended claims.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate aspects of the disclosure and together with the description, serve to explain the principles of the disclosure. Wherever possible, the same reference numbers will be used throughout the drawings to refer to the same or like parts.

FIG. 2A illustrates an exemplary distal end of a medical device in an expanded configuration;

FIG. 2B illustrates an exemplary injection of a compound between two tissue layers of the bladder wall;

DESCRIPTION

Figure 1:
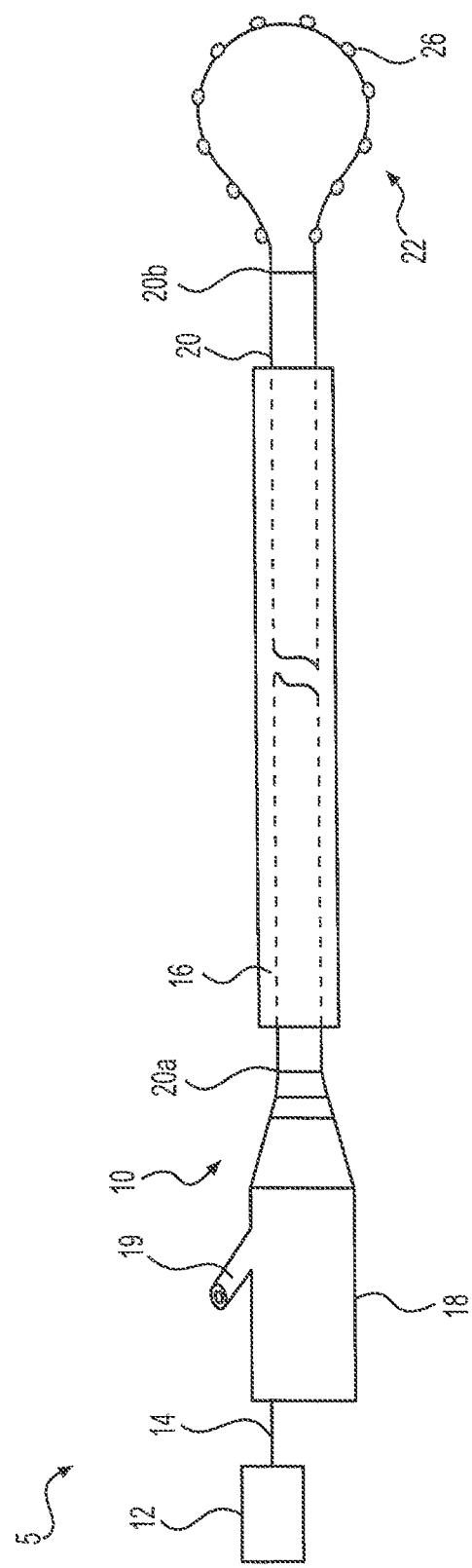
FIG. 1 illustrates a system for treatment of a bladder having a medical device, according to an aspect of the disclosure.

Particular aspects of the disclosure are described in greater detail below. The terms and definitions as used in the present application and as clarified herein are intended to represent the meaning within the present disclosure. The singular forms "a", "an", and "the" include plural reference unless the context dictates otherwise.

The terms "approximately" and "about" mean to be nearly the same as a referenced number or value. As used herein, the terms "approximately" and "about" should be generally understood to encompass ±10% of a specified amount, frequency, or value.

The present disclosure relates generally to compositions for treating tissue, such as tissue of a bladder, within a patient. For example, the present disclosure relates to compositions and methods for treating bladder overactivity. In some aspects, the compositions may be used to treat one or more other conditions related to overactivity. For example, the compositions may be used to reduce motility and/or peristalsis in the stomach or the GI tract. In another example, the composition may be used in a heart cavity or as a dermal filler.

Without being bound by theory, it is believed that the compositions disclosed herein may block certain substances that trigger nerves and lead to muscle irregularity, such as OAB. It is further believed that certain of these substances may be blocked by a hydro-dissection procedure, which separates the muscarinic and cholinergic receptors located in the mucosa (e.g., the urothelial and mucosal layers) from the detrusor muscle by injecting compositions disclosed herein into certain areas of the urinary bladder wall.

Exemplary medical devices and methods of injecting the compound into the bladder and other tissue are described in further detail below. Some examples of treating bladder overactivity by hydro-dissection are included in U.S. Provisional Patent Application No. 61/535,710, filed Sep. 16, 2011, U.S. Provisional Patent Application No. 61/677,590, filed Jul. 31, 2012, and U.S. patent application Ser. No. 13/599,916, filed Aug. 30, 2012, claiming priority thereto; as well as U.S. Provisional Application No. 61/799,260, filed Mar. 15, 2013, and U.S. patent application Ser. Nos. 14/211,247 and 14/211,440, both filed Mar. 14, 2014, claiming priority thereto, all of which are incorporated herein by reference in their entirety.

The composition may comprise any active agent(s) capable of preventing at least one, some, most, or all substances (e.g., ATP and Ach) from stimulating certain nerves and/or muscles in tissue. In some aspects, for example, the composition may inhibit and/or moderate stimulation of tissue via one or more mechanisms, including, but not limited to, serving as (1) a physical barrier, (2) a diffusion barrier, (3) a sink, and/or (4) a combination thereof, or via any other mechanism for inhibiting or moderating stimulation of tissue.

Physical Barrier

A compound, composition, material, etc., that may separate mucosal from detrusor tissue, e.g., in order to block or otherwise inhibit the transfer of one or more substances that may stimulate or over-stimulate tissue may serve as a physical barrier. Without being bound by theory, compositions of the present disclosure may inhibit biochemical pathways that trigger nerve firing, such as transfer of ATP, Ach, NO, PG, and/or NGF. In some aspects, the composition may serve as both a physical barrier and a diffusion barrier.

Diffusion Barrier

In some aspects, the composition may act as diffusion barrier. For example, the composition may diffuse and/or inhibit the transfer of substances like ATP, Ach, etc., between tissue layers. Exemplary compounds that may be used in the composition for forming a diffusion barrier include, but are not limited to, hydrophobic polymers, such as fluoropolymers, rubbers, polyolefins and other vinyl and vinylidene polymers or copolymers, anionic polymers such as polyelectrolytes (e.g., Ca binding, polyacrylic acid and methacrylic acid, etc.) and copolymers, ionic liquids, porphyrins, crown ethers, clathrates, oils, including oils that are liquid at body temperature (e.g., mineral oil, triglycerides, natural oils, and/or fluorinated oils), oils combined with polymers, and/or wax. In some aspects, the composition may serve as both a diffusion barrier and a physical barrier, as mentioned above.

Sink

In some aspects, the composition may serve as a sink to chemically or physically bind with substances like ATP, Ach, etc. to prevent them from binding to certain receptors in the body and/or participating in other biochemical reactions. For example, the composition may be used to prevent substances in the body from reaching nerves and/or detrusor muscle or other muscle tissue. The compositions may comprise one or more compounds that bind with a substance (e.g., ATP and Ach) that triggers nerves and/or muscles. Exemplary compounds that may be used in the composition serving as a sink include, but are not limited to, molecular cages (including, e.g., imprinted polymers), kinases, and other ATP binding proteins (for example, chaperones, ATPases, synthases, and other metabolic enzymes, including type II topoisomerases). Examples of agents to trap acetylcholine include, for example, acetylcholine binding protein.

Exemplary Compositions

In some aspects, the composition may comprise at least one polysaccharide compound such as, e.g., xanthan gum and/or alginate. Certain aspects of the disclosure are illustrated below through discussion of exemplary xanthan gum and alginate compositions, but the disclosure is not limited to xanthan gum or alginate.

Examples of compositions suitable for the tissue treatment disclosed herein may comprise biostable and/or biodegradable compounds in water miscible solvents. For example, poly(lactic-co-glycolic acid) (PLGA) dissolved in organic solvent may precipitate in tissue upon injection to form a polymer barrier. Other examples include suspensions, such as nanoparticles or microparticles and/or ground polymers combined with surfactant; naturally occurring polymers (e.g., tissue adhesives); thermally-sensitive compounds that may convert to gel as temperature increases or decreases (including, but not limited to, compounds that may be physically and/or chemically crosslinked in vivo); micelle solutions; liposomes; enzyme solutions (including, e.g., stabilized enzyme solutions); and/or particles that may be crosslinked or combined in vivo, e.g., via binding of covalently-attached molecules such as nucleic acids like DNA, proteins, and other molecules that may bind together.

The compositions may include at least one, some, or all of the below described properties. In some aspects, the compositions described herein may have significant efficacy due to spreading and/or hydrogel stiffness, and may enable long-term efficacy, e.g., as a barrier, due at least in part to slow degradation and/or absorption by the body. In some examples, the compound may be bioresorbable. The composition may degrade in tissue gradually and/or after a threshold amount of time. For example, the threshold amount of time may be greater than approximately a month, approximately two months, approximately six months, approximately nine months, approximately one year, approximately eighteen months, approximately two years, or longer.

The composition may have a viscosity suitable for injection into the body, e.g., at room temperature (approximately 25° C.). In some examples, the composition may have a viscosity ranging from approximately 50 centipoise (cP) to approximately 1800 cP at room temperature (~25° C.), such as from approximately 100 cP to approximately 1500 cP, e.g., from approximately 250 cP to approximately 1250 cP, or from approximately 500 cP to approximately 1000 cP. Upon injection into the body, the viscosity of the composition may decrease. In some examples, the viscosity of the composition may increase upon injection into the body.

The composition may comprise one or more compounds that may be hydrophilic. In some instances, a hydrophobic compound may be more likely to transition, e.g., diffuse, out of the targeted tissue pocket (e.g., between the mucosa and detrusor tissue) following injection. The composition and/or the medical device used for injecting the composition may be configured so that the composition is pushed at a force that enables dissection within the mucosa and detrusor plane, such that the composition spreads laterally in the bladder wall (e.g., between the two tissue layers of mucosa and detrusor) and does not push the urothelium in a direction perpendicular to the tissue layers (e.g., into or away from the interior of the bladder).

In some aspects, the compositions may be formulated to maintain a position in tissue and/or used in conjunction with a material to maintain a position in tissue. For example, hydrophobic compounds when injected into tissue may flow out of the injection site (e.g., since tissue area between mucosa and detrusor tissue is generally hydrophilic). In some aspects, the composition may be injected in combination with a polymer or polymer mixture that may act as a "stopper," e.g., a polymer stopper. The polymer stopper may comprise any suitable polymer material, including, but not limited to, biostable and/or biodegradable polymers, microbead slurry, and tissue glue (e.g., fibrin glue). In some examples, the composition may be included in a kit. For example, the kit may include the composition and a polymer or polymer mixture.

The composition may comprise one or more shear thinning compounds. For example, the viscosity may decrease during injection so that the compound may be injected through a suitable delivery device, such as, e.g., a needle. For example, the delivery device may include a narrow bore needle. Upon injection, the viscosity of the composition may decrease during bladder stretching so the composition maintains compliance with the bladder wall. At low or no shear, the composition may maintain its nominal viscosity which may ensure that the barrier created between mucosa and detrusor tissue may remain intact. The composition may maintain its viscosity after injection into tissue. In some aspects, the viscosity of the composition may increase after injection by absorbing water and/or ions (e.g., $Na^+$, $Ca^+$, $K^+$, etc.) from the surrounding tissue.

The composition may comprise a hydrogel. In some examples, the composition may comprise one or more polysaccharide compounds or a salt thereof. For example, the composition may comprise a cellulose compound such as carboxymethyl cellulose (CMC) or salt thereof (e.g., CMC) sodium, xanthan gum, alginate or a salt thereof (e.g., calcium alginate, such as Ca-alginate beads), chitosan, and/or hyaluronic acid. In some examples, the composition may comprise a mixture of hyaluronic acid and CMC, and/or may be crosslinked with a suitable crosslinking compound, such as butanediol diglycidyl ether (BDDE). In some aspects, the polysaccharide may be a homopolysaccharide or a heteropolysaccharide.

Table 1 below lists physical properties of some exemplary compounds. For implantable materials, the degradation rate generally refers to the residence time of the material in the body.

TABLE 1

|  | Molecular wt. (Da) | Viscosity (cP) | Degradation rate |
| --- | --- | --- | --- |
| CMC - low viscosity | 90,000 | 50-200 | 2-3 months |
| CMC - medium viscosity | 250,000 | 400-800 | 9 months-1 year |
| CMC - high viscosity | 700,000 | 1500-3000 | >1 year |
| Xanthan gum (1% wt.) | $1 \times 10^6$-$15 \times 10^6$ | 800-1200 | >1 year |
| Alginate | 10,000-600,000 |  | 2-3 months |
| Chitosan | 30,000-200,000 |  | 10-13 weeks |
| Hyaluronic acid | 5,000-20,000,000 (in vivo) |  | ~12 weeks |

The physical and/or chemical characteristics of the composition may be tailored for injectability into tissue and/or spreadability into adjacent tissues once injected. For example, the gelation kinetics, gel strength/viscosity, and/or the structure of the gel network may be adjusted to control injectability and spreadability. For example, in applications in which it is desirable for the compound to spread laterally in the bladder wall (e.g., between the two layers of mucosa and detrusor tissue) and not push the urothelium into a direction perpendicular to the tissue layers (e.g., into or away from the interior of the bladder), a relatively more fluidic, spreadable formulation may be appropriate.

The viscosity of the compositions may change over time, e.g., upon mixing. In some instances, composition may have a first viscosity immediately (and/or for a limited period of time) following mixing. The viscosity may increase over time (seconds, minutes, hours, etc.) to a second, higher viscosity. Additionally or alternatively, the viscosity of the compositions may change upon administration to the body, e.g., via injection. For example, the viscosity of the compositions may increase or decrease in viscosity in response to a stimulus or combination of stimuli in the body, such as, e.g., temperature, pH, or exposure to various chemical/biochemical substances. The increased viscosity may help to localize the formulation at the treatment site, e.g., such that the composition withstands the natural stretch of the bladder.

The gelation kinetics may be tailored for a desired delivery or release of the composition into tissue. Reaching gel strength generally refers to a gel reaching its maximum hardness, e.g., as measured by the elastic modulus G', as opposed to the viscous modulus G". The time required for a composition to reach its maximum gel strength may depend on its constituents. For example, the gel strength and/or viscosity of an alginate composition may depend on the concentrations of alginate, sequestrates, and/or crosslinking agents (e.g., crosslinking agents present in the composition or in the local environment) and/or the temperature of the composition. In some aspects, the gelation rate may increase with increasing temperature. In some aspects, gel strength may not follow a linear or non-linear relationship with respect to the concentration or range of concentrations of a particular constituent of the composition.

In some aspects, a calcium compound may be added to the composition to affect gelation kinetics. Calcium ions, e.g., from a suitable calcium salt such as, e.g., calcium sulfate dihydrate, calcium gluconoate, calcium lactate, and/or calcium chloride, may be released substantially simultaneously throughout entire material. The calcium ions may be released in a controlled manner. Relatively slower acting sources of calcium ions may alternatively be used to manipulate gelation kinetics. For example, calcium gluconoate (reaching its gel strength in approximately 2000 seconds) and/or calcium lactate (reaching its gel strength in approximately 500 seconds) may be used. It should be noted that calcium chloride generally reaches its gel strength in approximately 100 seconds. Calcium carbonate is generally insoluble in an aqueous environment at neutral pH. In some aspects, the composition may comprise a material or agent to facilitate release of calcium ions into solution. For example, a latent acid generator may be incorporated into the composition to lower pH, e.g., to at least partially solubilize the calcium carbonate to liberate calcium ions. The composition may form a gel within approximately 20-30 minutes after addition of the acid generator, such as within 5 minutes to approximately 20 minutes or approximately 10 minutes to approximately 15 minutes. In some aspects, the composition may comprise glucono delta lactone. For example, the lactone may hydrolyze to gluconic acid, thus lowering the local pH.

In some xanthan gum compositions according to the present disclosure, the presence of sodium may reduce viscosity at given concentrations. Viscosity may be mostly unaffected at a 0.5% concentration of xanthan gum solution. The viscosity of xanthan gum compositions may depend on the applied shear stress on the solution. For example, as the shear stress increases, the viscosity of the liquid may decrease (e.g., shear thinning).

One or more other parameters may affect or impact gel formation. Other factors affecting the gelation kinetics may include temperature, compounds and biochemical species present in the local environment, and local pH. For example, the properties of the polysaccharide molecules, e.g., branching into side groups, crosslinking, molecular weight, and/or chemical structure, may impact gel formation. For example, trisaccharide branches in xanthan gum may be relatively closely aligned with the polymer backbone. Xanthan gum may comprise a relatively stiff chain in the form of a single, double, or triple helix.

The gel strength of the composition may be modified (increased or decreased) in a variety of ways. For example, the temperature of the composition may be adjusted or regulated to increase or decrease gel strength. Further, for example, higher temperatures may decrease the viscosity of some compositions according to the present disclosure. Adjusting the pH of the composition may decrease or increase viscosity of some compositions according to the present disclosure.

The composition may comprise at least one sequestrating agent. Exemplary sequestrating agents include, but are not limited to, phosphonates, sodium trisphosphate (STPP), ethylene diamine disuccinate (EDDS), BAPTA, citric acid, EDTA, EGTA, [(carbamoylmethyl)imino]diacetic acid, disodium hydrogen phosphate, uridine monophosphate, trisodium citrate, sodium phytate, sodium hexametaphosphate (SHMP), oxalic acid, and ammonium oxalate. Sequestrating agents may additionally or alternatively be used in the compositions herein to adjust, modify, or manipulate gelation kinetics.

In some aspects, the compositions may comprise one or more preservatives. Exemplary preservatives suitable for the compositions disclosed herein may include, but are not limited to, sorbic acid, potassium sorbate, benzoic acid, and/or esters of hydroxybenzoic acid. Addition one or more preservatives may inhibit and/or decrease bacterial contamination of the composition.

In some aspects, the compositions may comprise one or more compounds or components that may increase resistance to biodegradation, e.g., to increase the longevity of the composition in tissue. For example, biodegradation may be decreased in the presence of a replenishable or constant supply of divalent cations and/or via covalent crosslinking.

Under some conditions, the composition may undergo a reversible ion exchange, e.g., between calcium ions in the composition and sodium ions in the blood. Once the calcium source of the composition is depleted, for example, sodium from the blood may replace calcium in the composition over time, which may degrade or reverse crosslinking. Sodium alginate is generally water soluble and may be flushed from the system. Providing a localized source of calcium ions may drive the equilibrium toward crosslinking, e.g., crosslinking alginate.

For example, a supply of divalent cations may readily diffuse from their ion source (e.g., a suitable crosslinking agent) to continuously or semi-continuously crosslink alginate, resulting in a network. As long as the ions are available to the alginate polymer chains, the alginate may undergo crosslinking. Under typical physiological conditions, the network may be resistant to biodegradation, e.g., due to a lack of hydrolytic or enzymatic chain breakages.

In some aspects, the composition may comprise Coaptite®. Coaptite® comprises calcium hydroxyapatite particles (generally ranging from about 75 μm to about 125 μm in diameter), which are suspended in a sodium carboxymethyl cellulose (CMC) gel carrier (~40% by weight). Coaptite®/CMC may be a viscous mixture. In order to mix Coaptite®/CMC in the composition, a needle comprising a side hole may be used to allow for injection of the Coaptite®/CMC, as discussed below.

Coaptite® may be combined with xanthan gum, alginate, and other polymers in the compositions. In some aspects, for example, the composition may comprise a combination of at least one hydrogel and Coaptite®, such as a combination of a hydrogel and Coaptite® particles. In some aspects, Coaptite® may be used to affect the formation of a barrier between tissue (e.g., between mucosa and muscle tissue). For example, a relatively faster degrading polymer (such as, e.g., alginate) could serve as a carrier, while the slower degrading Coaptite® particles may serve as the longer lasting filler in the injection site. In such an example, the barrier may be maintained, e.g., as the carrier degrades over time. In some aspects, a relatively slower degrading polymer may serve as a carrier, while the faster degrading Coaptite® particles may serve as the longer lasting filler in the injection site. Once the Coaptite® particles degrade, the carrier material may maintain a barrier in the tissue. In some examples, Coaptite® may act as a crosslinking agent.

Examples of Xanthan Gum Compositions

As mentioned above, in some aspects, the composition may comprise xanthan gum. An example of xanthan gum is Jungbunzlauer's Xanthan Gum FF (fine, 200 mesh, food & pharmaceutical grade). The xanthan gum may comprise pentasaccharide repeat units of glucose, mannose, and glucuronic acid (molar ratio 2:2:1). A polymer backbone of xanthan gum may comprise 1, 4-linked ß-D-glucose, e.g., similar in structure to cellulose. Trisaccharide side chains on alternating anhydroglucose units may distinguish xanthan gum from cellulose. Each side chain may comprise a glucuronic acid residue between two mannose units. At least one, some, or most of the terminal mannose units may include a 4, 6-linked pyruvate moiety; the mannose nearest the main chain may carry a 6-linked acetyl ester, and/or may be unsubstituted.

The composition may comprise xanthan gum mixed with a liquid, e.g., an aqueous solution, such as saline solution, e.g., a 0.85% saline solution or a 0.9% saline solution. In some aspects, the composition may comprise approximately 0.05% to approximately 1.5% of xanthan gum by weight, with respect to the total weight of the composition, such as approximately 0.1% to approximately 1% by weight, or approximately 0.6%, approximately 0.65%, or approximately 0.7% by weight, with respect to the total weight of the composition.

The xanthan gum and/or the composition comprising xanthan gum may be sterilized. Steam sterilization may help to increase stability of the composition. In one example, the xanthan gum and/or xanthan gum composition may be sterilized using steam sterilization. The steam sterilization may be performed at a temperature ranging from approximately 100° C. to approximately 130° C., such as a temperature of approximately 110° C. approximately 130° C., approximately 121° C., or approximately 120° C. Steam sterilization may be performed for a time ranging from approximately 5 minutes to approximately 30 minutes, such as from approximately 10 minutes to approximately 20 minutes, e.g., for approximately 15 minutes. Without being bound by theory, it is believed that sterilization of xanthan gum may decrease the molecular weight. For example, adding a salt may change the molecular weight during sterilization, and may increase the stability of the composition. For example, a xanthan gum composition may be prepared in a saline solution, e.g., by mixing the xanthan gum with a saline solution having a concentration ranging from approximately 0.8% to approximately 0.95%, e.g., a concentration of approximately 0.9%, followed by steam sterilization of the xanthan gum composition.

In some aspects, the xanthan gum compositions may be prepared by mixing xanthan gum with saline solution for a mixing time ranging from approximately 5 hours to approximately 12 hours, such as from approximately 6 hours to approximately 10 hours, e.g., a mixing time of approximately 6 hours, approximately 7 hours, or approximately 8 hours. For example, the xanthan gum compositions may be mixed for about 6 hours, e.g., at 330 rpm at room temperature.

Because xanthan gum is generally derived from bacteria, it may include certain endotoxins, e.g., bacterial endotoxins, that may be undesirable for the compositions disclosed herein. The endotoxin levels may increase with time of mixing and with increasing concentrations of xanthan gum. By limiting or minimizing the mixing time, the endotoxin levels in the xanthan gum compositions may be reduced. In some aspects, the composition may have an endotoxin content of less than approximately 600 Endotoxin Units, e.g., less than approximately 400 Endotoxin Units, or less than approximately 200 Endotoxin Units.

Compositions comprising xanthan gum may have a reduced viscosity at high shear (pseudoplastic) conditions during injection into tissue, e.g., the mucosa/detrusor tissue interface. Once the composition is injected, the composition may stiffen, e.g., with increased viscosity, to form a "stiffer" barrier. Compositions comprising xanthan gum may resist degradation. A lack of degradation and/or low degradability in vivo may result in long residence time of the composition within the body. For example, compositions comprising xanthan gum may have low degradability when compared to other polysaccharides, such as hyaluronic acid. In some aspects, the compositions comprising xanthan gum may retain their shape in the body (e.g., the shape formed after injection into tissue) over time. The xanthan gum composition may not change shape once administered into the body. For example, the xanthan gum composition may form an oval shape upon injection and may have substantially the same shape for six months to one year or more), and may not migrate significantly in tissue. Compositions comprising xanthan gum may thereby form and maintain a barrier, e.g., a physical barrier, at the target location (e.g., treatment site) for more than a year.

In some aspects, the composition may comprise xanthan gum and Coaptite®. As compared to xanthan gum alone, for example, the xanthan gum/Coaptite® composition may have increased hardness and/or may remain at the target location in the body for an increased amount of time.

Examples of Alginate Compositions

In addition or as an alternative to xanthan gum, the composition may comprise alginate. The alginate composition may include at least one, some, or all of the below described properties. For example, the alginate composition may have a viscosity suitable for injection (e.g., such that the composition is able to pass through a needle without early gelation). Upon administration into the body, e.g., via injection, the composition may have a relatively high viscosity (e.g., in order to maintain a physical barrier between the submucosa and the detrusor muscle), a relatively slow gelation time increasing viscosity to transition from relatively more liquid-like to relatively more gel-like (e.g., ranging from approximately 10 minutes to approximately 30 minutes, such as from approximately 15 minutes to approximately 20 minutes) to allow for a relatively high spreadability in tissue, and a relatively slow degradation rate (e.g., little to no degradation of the composition within approximately one year).

In some aspects, the alginate composition may comprise calcium. For example, the alginate composition may be prepared by mixing different alginate salts, e.g., sodium and/or calcium salt. For example, the composition may comprise Na-alginate, Ca-alginate, one or more calcium compounds or compound mixtures (including, but not limited to, e.g., salts such as calcium carbonate, calcium carbonate mixed with glucono delta lactone, calcium chloride, hydroxyapatite, and/or Ca particles, in desired ratios). The alginate composition may comprise a single type of calcium compound or a mixture of different calcium compounds. It should be noted that any of these calcium compounds may be used in the alginate compositions disclosed herein. Calcium ions from these compounds in solution may crosslink the alginate chains, e.g., forming a crosslinked network of alginate.

Any of the Na-alginate, Ca-alginate, and/or calcium compounds or compound mixtures may be in particle form, e.g., microparticles, nanoparticles, microsphere particles, or nanosphere particles. In some aspects, Ca particles may comprise calcium compounds that are insoluble at physiological pH, but may be solubilized (e.g., releasing calcium ions in solution) by lowering the pH, e.g., with localized reduction in pH. Examples of calcium particles suitable for the compositions disclosed herein include, but are not limited to, hydroxyapatite and calcium carbonate nanoparticles and microparticles. In some examples, the alginate composition may comprise Na-alginate, $CaCl_2$, and hydroxyapatite. Adding Ca-hydroxyapatite micro- or nanospheres to Na-alginate may increase the longevity of the composition's ability to serve as a physical barrier between tissue.

One example of an alginate composition for injection as a physical barrier may be a sodium alginate with induced gelation due to divalent and/or trivalent cation crosslinkers (e.g., $Ca^{2+}$, $Sr^{2+}$, $Ba^{2+}$, and/or $Al^{3+}$). Such a composition may be non-toxic, biocompatible, biodegradable, insoluble, and/or hydrophilic, and/or may exhibit swelling behavior (e.g., absorbing between approximately 2000 to approximately 300-fold own weight in water). In one example, the compound may comprise sodium alginate composed of unbranched copolymers of (1→4)-linked β-D-mannuronic acid (M) and α-L-guluronic acid (G) of varying ratios. Polyguluronic acid blocks may bind more effectively with calcium ions than polymannuronic acid blocks.

When selecting a compound and preparing a composition, the desired gel strength and immune response may be considered. In the case of alginate, for example, a higher content of guluronic acid (higher "G content") generally corresponds to stronger gel strength. Higher G alginate polymers tend to form more rigid gels, while alginate polymers with higher content of mannuronic acid (higher "M content") tend to form softer gels. Without being bound by theory, it is believed that higher M content may induce a faster immune response versus higher G polymers.

The composition may comprise any crosslinkers, including $CaCl_2$, $CaSO_4$, $CaCO_3$, calcium acetate, calcium ascorbate, and/or any compound that may serve as a source of divalent cations when dissociated in solution. The alginate affinity for a crosslinker may be correlated to the ionic strength of the cation. For example, $Mg^{2+}$ may have a lower ionic strength than $Ca^{2+}$, which may have a lower ionic strength than $Sr^{2+}$, which may have a lower ionic strength than $Ba^{2+}$.

In some examples, the alginate composition may comprise sodium alginate and calcium chloride. The ratio of Na-alginate to $CaCl_2$ may be about 1:2, and the sodium alginate may comprise from approximately 1.0% to approximately 5.0% by weight, with respect to the total weight of the composition, such as from approximately 2.0% to approximately 4.0% by weight, e.g., approximately 3.3%, approximately 3.5%, approximately 3.6%, or approximately 3.65% by weight, with respect to the total weight of the composition. In some aspects, the composition may comprise approximately 3.3 wt % of sodium alginate, and may form a gel upon injection into the body, e.g., in less than 15 minutes.

In at least one aspect, for example, the composition may comprise sodium alginate and calcium chloride in a 1:2 ratio, wherein the sodium alginate comprises approximately 1.5 wt % to approximately 2.5 wt %, with respect to the total weight of the composition, wherein the composition may be a relatively fluidic, spreadable composition. In applications in which it is desirable for the compound to push the urothelium in a direction perpendicular to the tissue layers (e.g., into or away from the interior of the bladder), relatively more gel-like composition may be appropriate. For example, in some aspects, the composition may comprise sodium alginate and calcium chloride in a 1:2 ratio, wherein sodium alginate may comprise approximately 3 wt % to approximately 3.65 wt %, with respect to the total weight of the composition. In some aspects, the compositions disclosed herein may augment the tissue structure upon injection, e.g., such that the compositions may act as bulking agents. In some aspects, the cellular network of the patient's tissue may be increased through the addition of one or more polymers, e.g., in addition to a polysaccharide compound as discussed above.

In some aspects, the alginate composition may comprise Coaptite®. Because mixing Coaptite®/CMC with an alginate solution in one syringe may cause the gelation process to start prematurely, risking the possibility of clogging the needle, Coaptite® may be added to an alginate composition through a double syringe in order to avoid needle clogging. The double syringe technique may be used to ensure that these two components come in contact with each other for a limited amount of time before injection.

In some aspects, collagen and/or one or more hydrophobic polymers may be added, e.g., to facilitate adhesion to cells. For example, alginate may have a hydrophilic limiting protein adsorption capacity (e.g., wherein proteins generally tend to adhere to surfaces that are hydrophobic rather than hydrophilic). Adding collagen and/or hydrophobic polymers may increase the ability for the alginate composition to adhere to cells upon injection in the body.

In some examples, gel strength may be increased in a variety of ways. For example, the composition may comprise one or more crosslinking agents, e.g., ionic and/or covalent crosslinking agents. In some aspects, the composition may comprise one or more covalent crosslinking agents such as, e.g., 2-[N-morpholino] ethanesulfonic acid hydrate buffer (MES), 1-hydroxybenzotriazole (HOBt), 1-ethyl-3-[3-(dimethylamino)propyl]carbodiimide (EDC), and/or adipic acid hydrazide (AAD). Additionally or alternatively, the temperature of the composition may be adjusted or regulated to increase or decrease gel strength. For example, higher temperatures may decrease the viscosity of the composition.

In some aspects, the composition may comprise alginate and calcium chloride. In some aspects, the composition may comprise alginate, calcium chloride, and Coaptite®. The alginate may include relatively high G-content sodium alginate, e.g., with ionic crosslinking. The composition may comprise one or more sequestrants. For example, the composition may comprise a sequestrating agent such as glycerol or a compound that provides a source of calcium ions.

The alginate composition may comprise high G-content sodium alginate with covalent crosslinking; high G-content sodium alginate with ionic crosslinking w/o sequestrate; high G-content sodium alginate with ionic crosslinking w/sequestrate and Coaptite®; high G-content sodium alginate with ionic crosslinking, sequestrate, Coaptite®; high G-content sodium alginate with covalent crosslinking, sequestrate, Coaptite®; high G-content sodium alginate with ionic crosslinking and Coaptite®; and/or high G-content sodium alginate with covalent crosslinking and Coaptite®.

In some examples, the composition may comprise calcium alginate, e.g., as a source of both alginate and calcium ions. The calcium alginate may be in particle form, such as beads of calcium alginate. The calcium alginate particles may be prepared from sodium alginate having a relatively high molecular weight, e.g., 200,000 g/mol, approximately 400,000 g/mol, approximately 800,000 g/mol, and/or 1,000,000 g/mol. For example, the sodium alginate may be mixed with a saline solution for a concentration of sodium alginate ranging from approximately 0.5% (w/v) to approximately 0.8% (w/v), e.g., a concentration of approximately 0.6% (w/v).

In some aspects, a sodium alginate solution may be mixed with a calcium salt, e.g., calcium chloride or other suitable calcium salt, to produce calcium alginate. For example, a stream of the alginate solution may be injected through a needle using a motorized syringe and cut using a jet of hydrated compressed air, forming alginate solution droplets that then may be crosslinked with calcium chloride. For example, the alginate solution droplets may be crosslinked in a 100 mM calcium chloride solution placed underneath the syringe. The particle diameter may be controlled by varying parameters such as, for example, the solution injection rate, airflow, and/or needle size. The mean diameters of the particles may range from approximately 500 nm to approximately 1000 μm, such as from approximately 750 nm to approximately 850 μm, from approximately 1.0 μm to approximately 750 μm, or from approximately 250 μm to approximately 750 μm, e.g., approximately 500 μm. In some aspects, for example, the mean diameter of the calcium alginate particles may be approximately 490 μm, approximately 505 μm, approximately 506 μm, or approximately 510 μm. In some examples, the beads may be produced so that they may degrade at a slower rate.

In some aspects, controlling the concentration of calcium used in crosslinking may affect the degradation rate of the composition. For example, a higher crosslink density may correspond to slower degradation times in the body. Further, the size of the particles may be related or correlated to the concentration of calcium. Increasing the concentration of calcium particles may strengthen the crosslinking network and slower the degradation rate of the composition. In some aspects, the particle distribution may be relatively broad, for example from about 10 μm to about 1000 μm, which may result in more efficient packing and/or higher overall viscosity of the composition. In some aspect, this may provide for a more effective or "packed" barrier between urothelium and detrusor. In some aspects, a relatively larger particle size may correspond to a relatively slower degradation rate.

In some aspects, different components of the composition may be mixed together at a predetermined time prior to injection, e.g., to ensure that the viscosity of the composition remains suitable for administration, such as by injection, e.g., via a delivery device such as a needle. For example, different components of the composition may be mixed by a physician (or other medical professional) less than about 5 minutes before injection, e.g., from approximately 15 seconds to approximately 5 minutes before injection, or less than 1 minute before injection, or less than approximately 30 seconds before injection. Mixing time may be depend on one or more parameters, including, e.g., the components of the mixture and the concentration of each component. In some aspects, a homogenous solution may be achieved for relatively more concentrated compositions by extended mixing. For example, Coaptite® may be mixed for an extended period of time due to its high viscosity. In some aspects, the mixing time may be proportional to the concentration of Coaptite® used. Molecular weight of a component also may affect mixing time. In some aspects, a relatively higher molecular weight may correspond to a relatively shorter mixing time, and a relatively shorter delay between mixing and injection. In some aspects, a relatively higher viscosity of the composition may correspond to a relatively shorter mixing time. In some aspects, a relatively higher concentration of calcium may correspond to a relatively shorter mixing time. Mixing times may vary. Without being bound by theory, it is believed that mixing time may affect how quickly the alginate will crosslink. In some aspects, for example, shorter mixing times may result in faster crosslinking. The mixing time may be less than about 30 minutes, e.g., from approximately 15 seconds to approximately 20 minutes, or approximately 1 minute. Mixing time may range from seconds to minutes, such as, e.g., from about 5 seconds to about 20 minutes, e.g., up to 1 minute or 5 minutes. In some aspects, the mixing time may be limited to no longer than 20 minutes, e.g., depending on the concentration and type of alginate used. Higher concentration and high G content alginate solutions, for example, may be mixed for times closer to about 20 minutes. Without being bound by theory, it is believed that the shorter the mixing time, the faster the mixed material will crosslink.

The different components may be mixed together in any suitable manner. For example, the components may be in separate syringes or other containers (e.g., a syringe containing an alginate solution and a syringe containing a calcium chloride solution), and combined using a Y-connector. If using syringes, the mixing achieved by passing liquid between two syringes (connected with a luer syringe connector) may be between approximately 2 passes and approximately 20 passes, e.g., approximately 5 passes between syringes.

In at least one aspect, the composition may comprise alginate (e.g., sodium alginate) and calcium chloride in about a 1:2 ratio (sodium alginate:$CaCl_2$) having an alginate concentration ranging from about 1.5 wt % to about 2.5 wt %, with respect to the total weight of the composition. least one aspect, the composition may comprise alginate (e.g., sodium alginate) and calcium chloride in about a 1:2 ratio (sodium alginate:$CaCl_2$) having an alginate concentration ranging from about 3.0 wt % to about 3.65 wt %, with respect to the total weight of the composition. The compositions may comprise a suitable solvent, such as, e.g., distilled water or saline solution.

Exemplary Devices and Methods

The compositions of the present disclosure may be formulated for delivery to a treatment site. For example, the compositions may be composition for delivery via injection through one or more needles and/or via a catheter (e.g., a rigid and/or flexible catheter tube). Any of the methods for treating bladder overactivity by hydro-dissection disclosed in U.S. Provisional Patent Application No. 61/535,710, filed Sep. 16, 2011, U.S. Provisional Patent Application No. 61/677,590, filed Jul. 31, 2012, and/or U.S. Provisional Application No. 61/799,260, filed Mar. 15, 2013, each of which is incorporated herein by reference in its entirety, may be used according to the present disclosure.

Those skilled in the art will understand that the systems, compositions, and methods described herein may be used to treat conditions of other organs, and conditions of the bladder other than bladder overactivity. For example, the present disclosure may be used in the treatment of bladder sphincter dyssynergia, stress incontinence, and/or painful bladder syndrome (interstitial cystitis), among other conditions. The same systems and methods may be employed in treating other organs such as, for example, the esophagus, stomach, intestines, colon, or the oral cavity, without departing from the scope of the present disclosure.

FIG. 1 illustrates an exemplary system 5 according to an aspect of the present disclosure. It is understood that other systems and devices may be used to deliver the compositions disclosed herein to tissue. As shown in FIG. 1, system 5 includes a medical device 10, at least one fluid source 12 in communication with, e.g., connected to, medical device 10 by way of at least one fluid conduit 14, and an outer sheath 16 surrounding at least a portion of medical device 10. Outer sheath 16 may be constructed from an insulating polymer compound such as polyamide, polyurethane, or any other suitable compound.

Medical device 10 includes an elongate member 20, a handle portion 18, and an end effector assembly 22. Elongate member 20 has a proximal end 20a and a distal end 20b. For purposes of this disclosure, "proximal" refers to the end closer to the device operator during use, and "distal" refers to the end further from the device operator during use. Handle portion 18 is disposed at proximal end 20a of elongate member 20 and end effector assembly 22 is disposed at distal end 20b of elongate member 20. End effector assembly 22 includes one or more injection units 26 for delivering compound to tissue layers of a bladder.

FIGS. 2A-2B illustrate a method for treating a bladder (or other organ) in accordance with an aspect of the present disclosure. In particular, FIGS. 2A-2B illustrate a method for treating bladder overactivity by separating two tissue layers within the bladder wall. Those of skill in the art will readily recognize that the principles of the disclosed aspects may have utility relative to any organ within a patient's body, such as the uterus, stomach, lung, etc.

Referring to FIGS. 2A and 2B, medical device 10 is inserted into the urethra of a patient after bladder emptying, and may be advanced to bladder 50 through outer sheath 16. Once a distal end of outer sheath 16 is positioned in bladder 50, end effector assembly 22 is advanced distally out of outer sheath 16. This may be achieved by, for example, pushing elongate member 20 distally relative to outer sheath 16, or pulling outer sheath 16 proximally relative to elongate member 20. Any suitable actuator on handle portion 18 may be used to effect deployment of end effector assembly 22.

Once end effector assembly 22 has been removed from outer sheath 16, inflation fluid may be delivered through lumen 28 to first expandable member 24 to inflate first expandable member 24 from a partially collapsed configuration (not shown) to an expanded configuration (FIG. 2A). When fully expanded, expandable member 24 may have a substantially spherical shape, positioning each injection unit 26 adjacent an interior surface of bladder wall 40 (FIG. 2A). It is understood that the expandable member may have alternative shapes, such as shapes mimicking the shape of the organ the medical device 10 is being inserted into. Further expansion of first expandable member 24 causes injector 30 of each injection unit 26 to pierce bladder wall 40. In some aspects, injector 30 may be configured to pierce the bladder wall 40 as deep as the mucosa-detrusor junction without penetrating the detrusor muscle. The penetration depth may be monitored in a number of ways. For example, injector 30 may be dimensioned to penetrate bladder wall 40 and deliver compound at a predetermined depth (i.e., injector 30 may be a single predetermined length). Alternatively, the injector 30 may include a flange, stop, or shoulder to press up against tissue to control the depth of penetration of the injector 30.

The procedure continues with the physician advancing an injection mechanism. Any suitable actuator on handle portion 18 may be used to advance the injection mechanism. In particular, the physician may move a tube relative to elongate member 20 in order to advance a second expandable member 36 from a retracted position within lumen 28 of elongate member 20 to a deployed position within interior space 24b of first expandable member 24. The mechanisms for extending second expandable member 36 into interior space 24b of first expandable member 24 may include, but are not limited to, self-expansion, pull-wires, etc.

Once second expandable member 36 is in the deployed position, inflation fluid may be delivered through a lumen to inflate second expandable member 36 from a collapsed configuration to an expanded configuration (FIGS. 2A and 2B). As second expandable member 36 expands, second expandable member 36 may come into contact with the one or more dispensers 32 associated with the one or more injection units 26. Further expansion of second expandable member 36 may exert a force on dispensers 32. Upon application of sufficient force, an impermeable membrane 32a of each dispenser 32 may rupture injecting compound from dispensers 32 into injectors 30 for delivery between tissue layers of the bladder. It is understood that dispensers 32 may take any number of shapes other than that disclosed in the figures, such as, for example, a bellows shape.

The composition may be in liquid form (e.g., comprising saline solution), gel form, or a liquid/gel that changes viscosity upon injection into tissue, e.g., solidifying into a more rigid gel or solid consistency, or decreasing viscosity into a more fluid consistency, as described above.

The composition may be injected into a space between two tissue layers 40a, 40b in bladder wall 40 to at least partially or completely separate portions of the two layers from each other. For example, the composition may be injected between the mucosal layer 40b and the detrusor layer 40a to create a semi-permanent barrier between the layers. Without being bound by theory, it is believe that this separation in tissue layers may at least partially biochemical pathways that cause or are associated with stimulating the detrusor muscle. The injections may be performed at multiple sites. For example, in some aspects the composition may be injected at sites spaced equidistantly from one another along bladder wall 40 so as to uniformly treat bladder 50. It is contemplated, however, that first expandable member 24 may be partially expanded, and end effector assembly 22 may be positioned adjacent a site of abnormal activity, to selectively treat that portion of bladder 50.

Other medical devices and methods of injection are contemplated. For example, in some aspects, the medical device may include one or more injection units having a needle array, e.g., a micro-needle array, in place of a single injector. In this manner, the medical device may be used to target a wider area of tissue, e.g., within the bladder or other organ. The composition may be delivered to the treatment site(s) through the injector onto tissue adjacent the needles without perforating through the bladder wall. This procedure may be performed for a set duration at varying amplitudes to increase the permeability of the mucosal layer (e.g., the urothelium).

In some aspects, the fluid dispenser 32 does not rupture, but rather fluid is releasable upon application of pressure which forces fluid through pores in the wall of the dispenser. The pores may be elastic or nonelastic, and may be holes, slots, or slits. Alternatively, the fluid dispenser 32 may remain sealed and the needle includes pores, slots, holes, or slits that open with increased pressure and convey fluid from the dispenser to the tissue.

EXAMPLES

The following examples are intended to illustrate the present disclosure without, however, being limiting in nature. It is understood that the present disclosure encompasses additional aspects consistent with the foregoing description and following examples.

Example 1: Composition Comparison

Compositions of xanthan gum, CMC, and different polymers (PEG, PLGA, Coaptite®) were prepared according to Table 2. Xanthan gum compositions were prepared by mixing xanthan gum with saline solution to produce xanthan gum concentrations of 1%, 0.5% and 0.25%

TABLE 2

| Compound | Compound conc. (wt %) | Solvent | Injection volume |
| --- | --- | --- | --- |
| Xanthan gum | 0.25% | saline 0.9% NaCl | 1 ml |
| Xanthan gum | 0.5% | saline 0.9% NaCl | 1 ml |
| Xanthan gum | 0.5% | saline 0.9% NaCl | 2 ml |
| Xanthan gum | 1% | saline 0.9% NaCl | 1 ml |
| CMC | 0.5% | saline 0.9% NaCl | 1 ml |
| CMC | 0.6% | saline 0.9% NaCl | 1 ml |
| CMC | 2% | saline 0.9% NaCl | 1 ml |
| PLGA | 5% | NMP/water 90%/10% | 1 ml |
| PLGA | 15% | NMP | 1 ml |
| Coaptite ® | 70% | 5% CMC in $H_2O$ | 1 ml |

A bladder fixture comprising porcine tissue was used to simulate injection of the compositions in the human bladder. The bladder fixture contained a base, a midpiece, a lid, and pins and bolts for securing the lid over the tissue. A porcine bladder was cut (butterflied) vertically from the dome to the urethra and the urethra was trimmed off. The bladder tissue was placed onto the vacuum chamber fixture above the midpiece (above the diaphragm) so that the interior bladder wall was facing up. The tissue was positioned by lightly placing it on pins (attached to the midpiece) so that the tissue covered the central cavity. Once in position, the operator pressed down on the tissue so that the pins pierced through the tissue. The tissue was secured by placing the lid above it and securing it with screws. The vacuum chamber fixture was placed next to a heating chamber. The fixture was elevated above the heating chamber so that gravity drained the fixture of saline through holes in the midpiece (connected to tubing), returning the saline back to the source. A heating chamber/bath was filled with water so that the coils were completely submerged and temperature was set to 47° C. Saline or a Krebs-Henseleit solution was placed in a glass container and placed into the heating chamber/bath. The tubing was submerged in the saline/Krebs-Henseleit solution in the container and the outlet was connected to the inflow for the vacuum fixture midpiece. The pump was turned on to move the heated saline into the gap between the diaphragm and tissue. Air was evacuated from the gap and a vacuum was applied to stretch the tissue. At this point, the tissue simulation setup was ready for injections.

An aliquot (1 ml or 2 ml) of each composition was injected between tissue layers of the bladder simulation. Once the injections were complete, a camera was set up above the tissue to record images during the experiment. The tissue was stretched using the vacuum for up to 1000 times, which corresponds to 83 days of filling and emptying in a porcine bladder (assuming a frequency of 12 micturitions per day). After the simulation, the tissue was taken off the fixture and each injection site was cut across the middle with a scalpel or blade. The tissue cross section was observed and measured under a microscope. The length, thickness, and cross-sectional areas were then measured for the injected mixture.

Figure 3A:
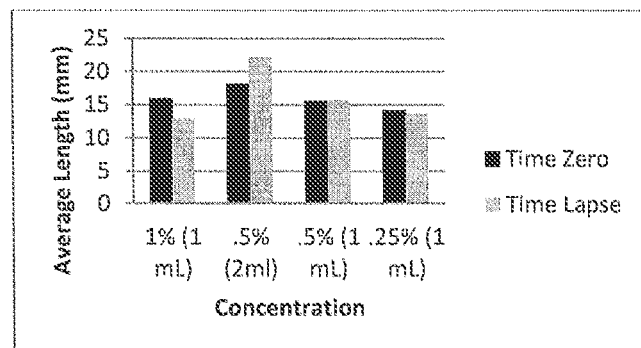
FIGS. 3A-C are graphical representations of the results of experiments on various compositions comprising xanthan gum, according to one or more aspects of the present disclosure.
Figure 3B:
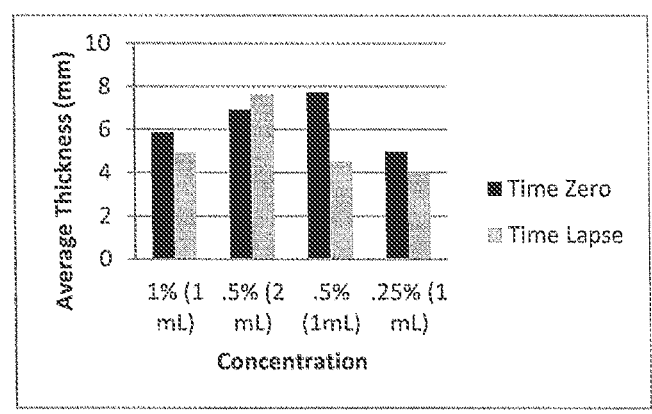
Figure 3C:
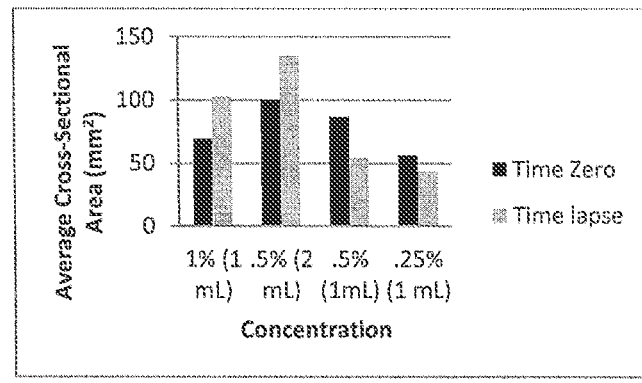

Results for the xanthan gum compositions are shown in FIGS. 3A-3C, showing the extent to which the compositions spread through tissue over time. FIG. 3A represents the average length (mm) of each composition within the tissue layers when the composition was first injected and after simulating 83 days within a human bladder. FIG. 3B represents the average width (mm) and FIG. 3C represents the average cross-sectional area (mm$^2$) for the same time periods. Averages were taken from the cross sections of multiple injection sites.

Figure 4A:
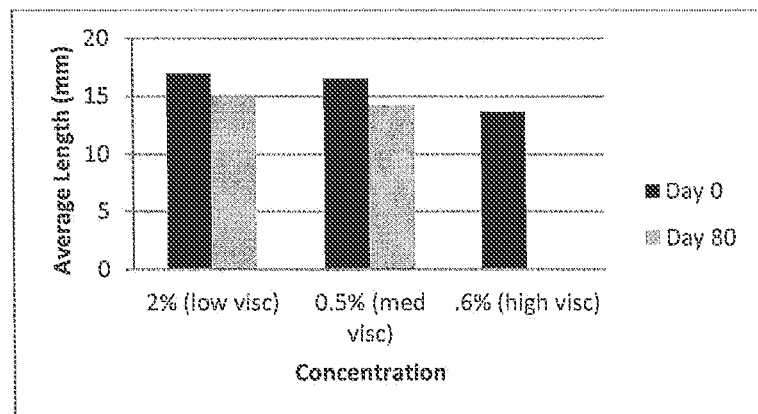
FIGS. 4A-C are graphical representations of the results of experiments on various compositions comprising carboxymethyl cellulose compositions, according to one or more aspects of the present disclosure.
Figure 4B:
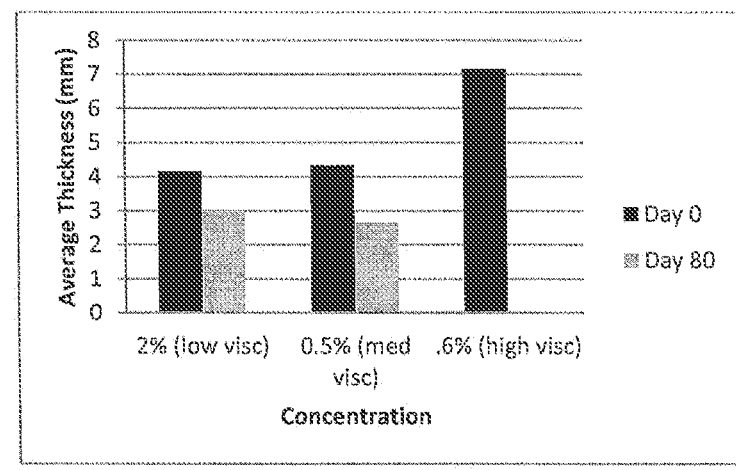
Figure 4C:
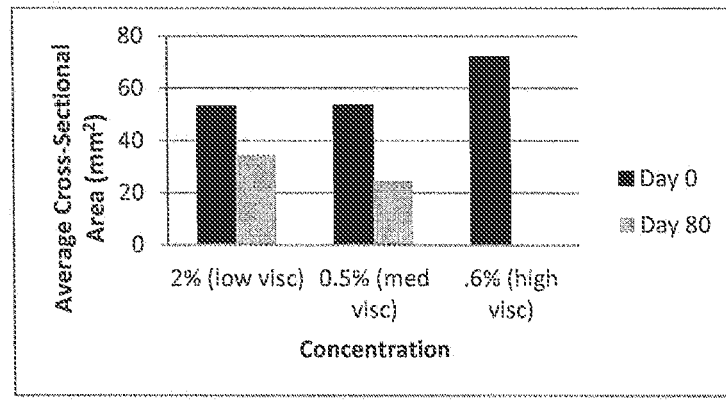

Results for the CMC compositions are shown in FIGS. 4A-4C, where FIG. 4A represents the average length (mm), FIG. 4B represents the average width (mm), and FIG. 4C represents the average cross-sectional area (mm$^2$) of each composition when the composition was first injected and after simulating 83 days within a human bladder.

Figure 5:
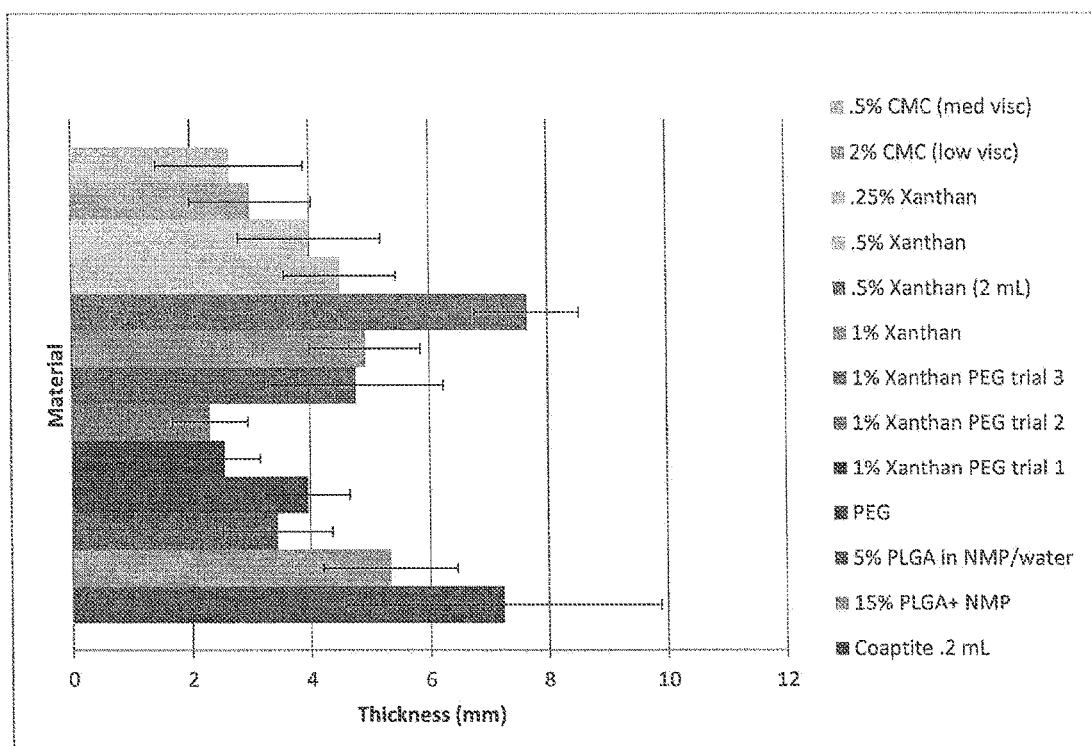
FIG. 5 is a graphical representation of the results of experiments on various compositions, according to one or more aspects of the present disclosure.

A comparison of average thickness of the injected composition samples, e.g., blebs, at the end of the simulated 83-day period of time is shown in FIG. 5, showing the average thickness of various compositions once injected and after simulating 83 days within a human bladder. The average length was measured in the lateral direction between the two layers of tissue. The average width was measured as the separation between the two layers or in the direction perpendicular to the two layers. The cross-sectional area may be measured as the area of the surface parallel with the layers of tissue. The thickness of the blebs ranged from about 2 mm to about 4 mm. The thickness of the detrusor muscle typically ranges from about 0.8 mm to about 3 mm. The target barrier thickness was the size of the detrusor thickness (assuming gel degrades over time and a barrier needs to be maintained for at least a year after injection).

Example 2: Alginate Compositions

Example 2A: Alginate-Calcium Chloride Composition

Sodium alginate was added to distilled water and mixed (15-20 minutes) in a glass beaker. Calcium chloride was added to distilled water and mixed in a separate beaker. A 0.75 ml aliquot of each solution was added to individual 3-ml syringes. The two syringes were connected using a Y-shaped syringe connector. A backstop needle was connected and both syringes pushed simultaneously (if alginate and calcium chloride are not mixed thoroughly, phase separation may occur) into bladder tissue between submucosa and detrusor tissue layers. The mixture should be injected quickly as gelation may occur quickly, e.g., instantaneously. In this experiment, gelation initiated instantaneously, with maximum gelation observed after about 15 min.

Example 2B: Coaptite®-Alginate-Calcium Chloride Composition

Coaptite® was transferred into new 3-ml syringes and mixed with sodium alginate (SA) in a separate syringe using a syringe connector. (Note that mixing Coaptite® and calcium chloride mixture instead does not change injectability.) The contents of each syringe into were mixed back and forth approximately ten times. One syringe containing the Coaptite®-SA mixture was connected to another syringe containing $CaCl_2$ using a Y-shaped syringe connector. The contents were expelled simultaneously through a backstop needle into bladder tissue between submucosa and detrusor tissue of a simulated bladder (see discussion in Example 1). Gelation occurred after about 15 minutes.

Example 2C: Molar Ratios Alginate:Calcium Chloride

Different molar ratios of calcium chloride to sodium alginate were tested and observations provided as described in Table 3.

TABLE 3

| Molar ratio ($CaCl_2$:SA) | Observations |
|---|---|
| 1:3 | Not much gelation; liquid phase dominant; easily passed through needle |
| 1:2 | Gelation time varied between concentrations of sodium alginate; formed gel with slight thickness |
| 2:1 | Gels in syringe; clogs needle; formed very thick gel |
| 10:1 | Gelation occurred immediately in syringe; clogs needle; formed very thick gel |

Increasing calcium chloride ratio appeared to speed up gelation process with visible changes in gel thickness. Increasing calcium chloride concentration tended to increase membrane thickness due to the increase in calcium ions diffusing into gel and sodium alginate. Any more increases to ratio would start approaching maximum potential of gel thickness (e.g., not injectable). Increasing sodium alginate decreased gel thickness and gelation. Increasing sodium alginate concentration resulted in a decrease in membrane thickness due to increasing gel density and not enough space for calcium ion diffusion. A 1:3 ratio $CaCl_2$:SA was found to be mostly liquid, very limited thickness, very injectable, whereas a 10:1 ratio of $CaCl_2$:SA was found to be mostly gel, high thickness, and not injectable. It was determined that a ratio of about 1:2 provided suitable characteristics in gel spreadability, desired gel thickness, desired gelation time, and injectability.

Different concentrations of sodium alginate and appropriate calcium chloride (to maintain molar ratio) were mixed in distilled water with observations provided in Table 4.

TABLE 4

| Conc. sodium alginate (wt %) | Observations |
| --- | --- |
| 1.5 | Slightly viscous but more fluidic; liquid phase dominant |
| 2 | More viscous but still fluidic |
| 3 | Liquid phase gone; mostly in gel phase; not very stiff |
| 3.5 | Stiffer and stronger gel |
| 3.6 | Same stiffness as 3.5 wt % |
| 3.65 | Becoming challenging to push through needle; beginning to see needle clogging |
| 3.75 | Harder to push through needle; needle partially clogged |
| 3.8 | Difficult to push through needle; requires extra exertion; needle became clogged |
| 4 | Very difficult to push through needle; gelation occurred too quickly; formed thick and strong gel; slightly weak |
| 4.5 | Weaker but thicker gel; passed through needle better |

Example 3: Comparison of Xanthan Gum and Alginate Compositions

A 0.65% wt. xanthan gum composition was prepared by adding the appropriate amount of xanthan gum to 100 ml of 0.9% saline solution in a large glass container. Xanthan gum powder was added slowly during vigorous stirring to ensure complete dissolution of xanthan gum. This solution was thoroughly mixed on a stir plate at around 330 rpm for 6-15 hours at room temperature. A 3.6 wt % sodium alginate composition also was prepared by adding the appropriate amount of alginate powder to 100 ml of distilled water and letting the mixture stir for about 30 minutes to form a highly-gelled composition. One drop of green tattoo dye was added to each mixture to distinguish between the material and tissue in the bladder. The xanthan gum composition appeared to be more flexible with the tissue of the simulated bladder in comparison to the alginate composition. Sodium alginate appeared to bulk up the tissue to a greater degree, forming a relatively rigid/stiff bleb, but tended to leave tissue upon exerted force. The two compositions had about the same level of ease with injectability, e.g., minor resistance but relatively easy to inject. Gelation occurred in no more than 15 minutes.

Example 4: Composition Solvents

Example 4A: Saline

An alginate/calcium chloride composition was prepared by mixing sodium alginate and calcium chloride in saline solution instead of distilled water, e.g., to 1) simulate physiological conditions, and 2) experiment in delaying gelation time for using higher ratios of calcium chloride, e.g., to acquire higher gel strength/thickness. There is evidence that gelation is dependent upon calcium ion interaction with alginate binding zones. Also, inhibiting interaction using foreign molecules, such as saline, could delay gelling. Gelation could potentially be inhibited using glycerol while allowing for homogenous gel mixing.

The composition (0.65% xanthan gum) was prepared by adding the appropriate amount of xanthan gum to 100 ml of saline solution in a large glass beaker. The beaker was left to mix on a stir plate at 330 rpm for 6-15 hours at room temperature. Increasing saline content was observed to increase gelation rate (gelation was found to start in the syringe/needle). Saline solution may provide a potential mechanism to increase gelation time for other compositions. It is possible that saline may hinder the ability of ions to crosslink alginate chains, resulting in a longer gelation period. Saline may also cause phase separation if more is present in mixture in comparison to alginate. A ratio of 1:1 was demonstrated to show this phase separation occurring. Phase separation was observed where the alginate component of the mixture had separated from the solvent and/or crosslinker component. This was observed due to the green-dyed gel being separated from the other off-white component.

Example 4B: Coaptite®

The composition from Example 4A was mixed with Coaptite® in a 1:1 ratio to alginate, e.g., to test the ability of the composition 1) to form a strong barrier, and 2) to create a highly networked material. Compositions comprising relatively low ratios of $CaCl_2$:SA (e.g., 1:2) were not injectable. Most of the Coaptite® remained in the syringe/needle and clogged the needle. The mixture became too thick in the syringe/needle, and did not gel. Using Coaptite®, e.g., as a crosslinking agent, may provide a better hydrogel network due to its slower gelation time.

Example 5: Xanthan Gum Compositions

Samples of xanthan gum (0.750 g) were mixed with 150 mL of 0.9 wt % saline solution in a large glass beaker with a stirring rod at 330 rpm at room temperature to obtain 0.65 wt % xanthan gum in saline. To determine the amount of mixing time necessary for preparing homogeneous solutions and the effect, if any, on endotoxin levels, three solutions were prepared, each having a xanthan gum concentration of 0.65%. The solutions were mixed for (1) approximately 30 minutes, (2) approximately 12 hours, and (3) approximately 16 hours. mixing was determined as the stage at which the solution did not contain any visible particles (visible to the naked eye).

TABLE 5

| Mixing Time (hours) | Observations |
| --- | --- |
| 0.5 | More mixing time needed in order to ensure visible homogeneity |
| 12 | Visibly homogenous at less than or equal to approximately 7.5 hours |
| 16 | Visibly homogenous between approximately 6 hours and approximately 10 hours |

Other aspects of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating tissue of a patient, the method comprising injecting a composition between a first layer of tissue and a second layer of tissue of an organ in the patient in need thereof;
   wherein the composition comprises xanthan gum by weight, with respect to the total weight of the composition and wherein the xanthan gum has a molecular weight between $1 \times 10^6$ and $15 \times 10^6$ Da, and wherein the xanthan gum has a viscosity between 800 and 1200 cP; and
   wherein the composition separates the first layer of tissue from the second layer of tissue of the organ.

2. The method of claim 1, wherein the organ is a bladder, and
wherein the method includes an initial step of detecting one or more locations of abnormal contraction of the bladder, and wherein the step of injecting the composition between the first layer of tissue and the second layer of tissue includes injecting the composition between the first layer of tissue and the second layer of tissue at the one or more locations of abnormal contraction of the bladder.

3. The method of claim 2, wherein at least one of the first layer or the second layer of tissue is a detrusor muscle tissue.

4. The method of claim 3, wherein the contraction of the detrusor muscle tissue is reduced after the composition is injected.

5. The method of claim 1, wherein the composition has a first viscosity before injection into the organ, and a second viscosity higher than the first viscosity after the composition is injected into the organ.

6. The method of claim 1, wherein the composition further comprises at least one polysaccharide compound that is chosen from alginate, pectin, a glycosaminoglycan, carboxymethyl cellulose, chitosan, a salt thereof, or a combination thereof.

7. The method of claim 1, wherein the composition further comprises alginate, and wherein the composition further comprises at least one calcium compound.

8. The method of claim 7, wherein a molar ratio of the calcium compound to the alginate ranges from about 1:1 to about 1:3.

9. A method of treating a bladder of a patient, the method comprising:
detecting one or more locations of abnormal contraction of the bladder;
injecting a composition at the one or more locations of abnormal contraction between a first layer of tissue and a second layer of tissue of the bladder in the patient in need thereof; and measuring an average thickness of the injected composition at a time greater than approximately two months after the injection;
wherein the composition comprises xanthan gum, the concentration of the xanthan gum ranging from approximately 0.05% to approximately 1.5% by weight, with respect to the total weight of the composition; and
wherein the composition separates the first layer of tissue from the second layer of tissue.

10. The method of claim 9, wherein the first layer of tissue is a mucosal layer, and the second layer of tissue is a muscle layer.

11. The method of claim 9, wherein the composition further comprises alginate, and wherein the composition further comprises a calcium compound, the composition having a molar ratio of calcium compound to alginate of about 1:2.

12. The method of claim 9, wherein the composition further comprises calcium alginate.

13. The method of claim 9, further comprising:
mixing the xanthan gum with a second component of the composition less than approximately 20 minutes before injecting the composition.

14. A method of treating a bladder of a patient, the method comprising:
detecting one or more locations of abnormal contraction of the bladder; and
injecting a composition at the one or more locations of abnormal contraction between a first layer of tissue and a second layer of tissue of the bladder in the patient in need thereof;
wherein the composition comprises xanthan gum having a concentration ranging from approximately 0.05% to approximately 1.5% by weight, with respect to the total weight of the composition, a molecular weight of between $1 \times 10^6$ and $15 \times 10^6$ Da, and a viscosity between 800 and 1200 cP;
wherein the composition separates the first layer of tissue from the second layer of tissue; and
wherein at least one of the first layer of tissue or the second layer of tissue is a detrusor muscle tissue.

15. The method of claim 14, further including at least one polysaccharide compound chosen from alginate, pectin, a glycosaminoglycan, carboxymethyl cellulose, chitosan, a salt thereof, or a combination thereof.

16. The method of claim 14, wherein the composition has a first viscosity before injection into the bladder, and a second viscosity higher than the first viscosity after injection into the bladder.

17. The method of claim 14, wherein the composition forms a gel between the first tissue layer and the second tissue layer.

18. The method of claim 17, wherein the composition forms a gel within about 20 minutes after injection into the bladder.

19. The method of claim 9, wherein the concentration of xanthan gum is approximately 1% by weight, wherein the xanthan gum has a molecular weight between $1 \times 10^6$ and $15 \times 10^6$ Da, and wherein the xanthan gum has a viscosity between 800 and 1200 cP, and
wherein the composition further includes at least one of a carboxymethyl cellulose with a molecular weight of approximately 250,000 Da and a viscosity between 400 and 800 cP or a carboxymethyl cellulose with a molecular weight of approximately 700,000 Da and a viscosity between 1500 and 3000 cP.

* * * * *